United States Patent
Malessa (10) Patent No.: US 9,125,825 B2
(45) Date of Patent: Sep. 8, 2015

(54) FREEZE-DRIED MOLDED ARTICLE CONTAINING MAGNESIUM ASCORBYL PHOSPHATE

(75) Inventor: Ralf Malessa, Essen (DE)

(73) Assignee: Medskin Solutions Dr. Suwelack AG, Billerbeck (DE)

( * ) Notice: Subject to any disclaimer, the term of this patent is extended or adjusted under 35 U.S.C. 154(b) by 520 days.

(21) Appl. No.: 12/763,632

(22) Filed: Apr. 20, 2010

(65) Prior Publication Data
US 2010/0272834 A1 Oct. 28, 2010

(30) Foreign Application Priority Data
Apr. 22, 2009 (EP) .................................... 09158475

(51) Int. Cl.
| | |
|---|---|
| *A61K 36/82* | (2006.01) |
| *A61K 31/34* | (2006.01) |
| *A61K 9/20* | (2006.01) |
| *A23L 1/00* | (2006.01) |
| *A61K 8/67* | (2006.01) |
| *A61K 8/73* | (2006.01) |
| *A61K 9/00* | (2006.01) |
| *A61Q 19/00* | (2006.01) |

(52) U.S. Cl.
CPC .................. *A61K 9/2095* (2013.01); *A23L 1/00* (2013.01); *A61K 8/676* (2013.01); *A61K 8/733* (2013.01); *A61K 9/0014* (2013.01); *A61K 9/0056* (2013.01); *A61K 36/82* (2013.01); *A61Q 19/00* (2013.01); *A61K 2800/84* (2013.01)

(58) Field of Classification Search
None
See application file for complete search history.

(56) References Cited

U.S. PATENT DOCUMENTS 6,497,887 B1 * 12/2002 Zecchino et al. ............. 424/401

FOREIGN PATENT DOCUMENTS

| | | |
|---|---|---|
| DE | 2008/020066 | 2/2008 |
| FR | 2886845 | 12/2006 |
| FR | 2886845 A1 * | 12/2006 |
| WO | 2009/014347 | 1/2009 |

OTHER PUBLICATIONS

Makingcosmetics.com. Retrieved from the internet on Jan. 16, 2012. Aug. 1, 2008. <http://www.makingcosmetics.com/fact-sheets/fact-sheet-vitamin-c-magnesium-ascorbyl-phosphate.pdf>. 1 page.*
Naturalfairness. Jan. 20, 2005. Retrieved from the internet on Jan. 17, 2012. <http://naturalfairness.talkware.co.uk/blog/_archives/2005/1/20/267568.html>.7 pages.*
Website document entitled: "Paula's Skincare: Magnesium Ascorbyl Phosphate". (available at http://paulaschoice.com/cosmetic-ingredient-dictionary/definition/magnesium-ascorbyl-phosphate). Downloaded from website Sep. 11, 2014.*

* cited by examiner

*Primary Examiner* — Chris R Tate
*Assistant Examiner* — Russell Fiebig
(74) *Attorney, Agent, or Firm* — Ballard Spahr LLP (57) ABSTRACT

The invention relates to freeze-dried molded articles containing magnesium ascorbyl phosphate and alginate as well as optionally one or more active substances and/or auxiliary substances. Furthermore, the invention relates to methods for manufacturing these freeze-dried molded articles, the combination of such freeze-dried molded articles in kit-of-parts arrangements together with aqueous solutions, as well as the use of the freeze-dried molded articles and the kit-of-parts combinations for pharmaceutical and cosmetic application.

12 Claims, 3 Drawing Sheets

FREEZE-DRIED MOLDED ARTICLE CONTAINING MAGNESIUM ASCORBYL PHOSPHATE

BACKGROUND OF THE INVENTION

The invention relates to freeze-dried molded articles containing magnesium ascorbyl phosphate and alginate as well as optionally one or more active substances and/or auxiliary substances. Furthermore, the invention relates to methods for manufacturing these freeze-dried molded articles, the combination of such freeze-dried molded articles in kit-of-parts arrangements together with aqueous solutions, as well as the use of the freeze-dried molded articles and the kit-of-parts combinations for pharmaceutical and cosmetic application.

In the pharmaceutical and cosmetic application and administration of active ingredients and care substances or other active substances, the selection of provision of the suitable form of administration, in particular, plays a central role for the application of the active and/or care substances. Factors such as, e.g. reproducible and effective contents of active substances, a high degree of safety in storage and application, good and reproducible availability of the active substances after application are factors that must in this case be taken into account; optionally, a stabilization against degradation or decomposition of the active substances contained can be of importance, as well as the provision in a form of administration that is optimally adapted to the respective purpose of application. The choice of the suitable form of application in this case particularly depends on the type and place of application, the target group of end users and their special characteristics, the type and quantity of the dosage of the active substances or also, for example, the physical and biochemical characteristics of the active substances, in particular with regard to their biological availability and their systemic mode of action.

The stabilization and preservation of the preparations constitutes a particularly important aspect in the administration of active ingredients and substances or cosmetic care substances. Particularly long-lasting and stable form of administration are water-free or solid and dry preparations, which furthermore have particularly good storage and transport properties. Especially with regard to administration systems in dried or dry form, the central issue in the administration on and in the human body that arises is the dissolution or solubility of the form of administration and thus the release and availability of the active ingredients, care and active substances. The requirements with regard to the kind, rate and place of dissolution vary with the specific application, the substances to be applied as well as, if applicable, other factors to be taken into consideration.

In particular in the cosmetic application of active substances, forms of administration of particularly desired which makes the external administration of active ingredients, active and care substances on the skin and hair possible in an optimum manner, but the external application also plays a large role in the pharmaceutical application of active substances, in addition to the oral administration of active substances.

Water-free forms of administration are an appropriate means for the quick and specific application of active substances, in particular those that have a certain instability with regard to external factors, such as moisture, oxidation and temperature. Dry preparations that have a particularly fast and complete dissolution behavior are of particular interest. This is particularly relevant in making moisture-unstable active substances available, as well as generally in oral application of active substances that are to be absorbed, for example, via the oral mucosa, or for users who have problems swallowing tablets or capsules.

Other drawbacks of known dry forms of administration, such as powder mixtures, granules, tablets or capsules are in particular the frequently poor or slow solubility and thus the delayed active substance release, the high proportion of auxiliary and filler substances, which are inactive but necessary for processing, the regularly poor suitability for external application as well as an insufficient disability and thus safe handling or problems with application by the end user.

A suitable and known manner of providing active substances in a readily soluble, dry form of application or dosage is to disperse the active substances in a system of carrier substances and to subject this mixture to freeze drying. Mostly, such substances are selected as carrier substances that have a good dissolution or swelling behavior and which, through swelling, enable a good texture formation, so that the dissolved active substance system, or the active substance system dispersed in the swelling agent, can be used directly as a form of application. Such systems, because of their good solubility, are known and suitable for providing oral forms of application, as well as for producing cosmetic or pharmaceutical forms of administration for external application. In this case, there in a increasing interest in providing so-called single-unit forms of application which enable a simple and precise application of a dose of an active substance for the end user. Single-unit forms of application in this context are understood to be application systems, which in contrast to powders or granules contain the desired and required quantity of active substance per application unit in a single application unit, such as tablets or capsules, without, however, having the drawbacks of difficulties with regard to swallowing, poor solubility or lack of suitability for external application.

For both cosmetic and pharmaceutical application of single-application molded articles, relatively large molded articles of a uniform shape and size are preferred because in contrast to powders or small pellets and granules, they can be handled more easily by the end user, so that the intention is to provide molded articles of such a size that permit a single dosage form per application. Moreover, larger molded articles, which can, for example, be given a colored design, also leave a stronger aesthetic impression.

Increasingly, larger-format configurations of such single-unit forms of application stabilized by drying are becoming interesting for oral and/or external administration of active substances which are characterized by a particularly quick, reliable and complete dissolution behavior, if possible without any inhomogeneous, incompletely dissolved residues.

The dissolution behavior of a molded article is a complex function of physical/chemical parameters. The physical basis for the kinetic aspect of the hydration process is constituted by individual parameters, such as swelling capability of the carrier substances used, structural integrity of the molded article while swelling, pore size, capillary forces caused by the pore structure, components of the recipe altering surface tension, density of the molded article etc. Apart from pure "solubility", or, in the case of polymer-based carrier substances, the "swelling capacity", the mechanical stability of the molded article in this case plays a pivotal role. If the polymeric material swells too quickly, the molded article loses its physical integrity too quickly and collapses. The molded article melts while moisture is added, in most cases while forming "inner" areas with a lower moisture content that have not yet swelled.

If the stabilizing interactions within the material are too large, the material may swell while water is added, but then decomposes only under mechanical stress, such as by mechanical stirring, rubbing, squashing or massaging. A compromise, sufficient mechanical strength for compensating the weight increase while swelling with subsequent rapid hydration is very difficult to achieve.

Known rapidly soluble dosage forms, e.g. for oral application of active substances are produced by the companies R. P. Scherer and Cardinal Health under the brand name Zydis®, wherein the liquid active substance composition is filled into a blister pack and freeze-dried in the final packaging. This method is necessary because of the low mechanical stability of the readily soluble oral dosage forms that can be obtained thereby. The lack of mechanical stability, however, is disadvantageous with regard to the external application. Moreover, molded articles to be handled individually with sufficient mechanical stability for use as single-unit forms of application with a particularly rapid and complete dissolution behavior are obviously not available. Moreover, a method for freeze drying in blister packs is technically complex and cost-intensive, and the forms of administration that can be obtained thereby are limited to conventional blister packs with regard to their presentation and combination possibilities, which is undesirable in particular with regard to cosmetic applications.

Other rapidly soluble preparations that are also freeze-dried in blister packs because of a lack in mechanical stability are the subject matter of U.S. Pat. No. 4,758,0598 and U.S. Pat. No. 4,305,502.

DE 69727922 is distinct therefrom by producing oral, rapidly soluble forms of administration with a higher stability, which contain relatively high contents of fillers, such as, e.g., mannitol as well as binding agents, such as, e.g., alginate, and which are not obtainable by means of expensive and complicated freeze-drying methods. The oral dosage forms thus obtainable are characterized by a solubility of <15 seconds. However, it is not apparent from DE 69727922 that molded articles with a sufficient mechanical, which is required in particular for external application, are obtainable by means of the method described. Moreover, the issue of quick and complete dissolution without any mechanical influence and, in the process, without the formation of Inhomogeneous, non-swelled inner areas, is not broached. Since the dosage forms described in DE 69727922 are only intended for oral application, such a special dissolution behavior is not really relevant, because the actions of the tongue and the palate inevitably constitute a mechanical influence, which, if necessary, support non-uniformly dissolved areas in their continued dissolution. Other known methods for providing rapidly soluble forms of application of active substances that can be used as single-unit dosage forms with a certain size are described in U.S. Pat. No. 5,405,616 and DE 4201179. The carrier materials used therein preferably are based on proteins. The pellets are produced by dripping dispersions of the protein scaffold-forming agents and optionally cosmetic or pharmaceutical active substances into cryogenic inert liquids, preferably liquid nitrogen, and subsequently separating and freeze-drying the frozen pellets. However, the presence of protein scaffold-forming agents, in particular of collagen or collagen derivatives, is necessary in order to form pellets under these conditions, because only the aforementioned protein scaffold-forming agents are able to form stable pellets under these conditions. However, proteinogenic carrier materials are unsuitable for achieving a particularly quick and complete dissolution behavior without any residues of swelled areas and, in particular, without any mechanical influence, as is desired in this case, because of the high requirements with regard to the intramolecular stabilization of the composition in the dripping method used.

Similar problems result from the method for producing porous galenic particles described in U.S. Pat. No. 5,843,347, which are supposed to be obtained in sizes of up to 5 mm, according to the description. In the method used herein, a mixture of the active substances is extruded in a matrix and cut into particles with the desired size, which subsequently form the porous molded articles by freeze drying. However, the exemplary embodiments merely show that so-called microspheres with diameters of up to a maximum of 1.5 mm can be obtained. This can be ascribed to the use according to the invention of an extrusion and cutting method that requires a certain mechanical stability of the extruded mass. This can generally be obtained by a relatively high content of scaffold-forming polymers or carrier substances and stabilizers or fillers. However, if only small amounts of stabilizing carrier or auxiliary substances are used as compared with the content of active substances, then very small-format microspheres can be obtained, as is shown in this document.

Another method that provides the production of readily soluble molded articles loaded with active substances is the subject matter of WO 05/073296 and WO 04/011537, with neither document giving any specific statements with regard to the kind or, in particular, rate of the dissolution. Especially the particularly rapid and residue-free dissolution without mechanical influence is not mentioned.

A rapidly soluble large-format molded article that is suitable for the external administration of active substances is the subject matter of DE 10248314, which was also published as WO 2004/035023. The forms of application that can be obtained by the method described therein are large-formal molded articles of a regular shape loaded with active substances, which articles can be obtained by a freeze-drying method of an active substance-scaffold-forming agent mixture poured into molds. The molded articles that can be obtained according to the described method are characterized by good mechanical stability and a high dissolution rate of <4 minutes, with the latter being fundamentally dependent, however, on the respective content of scaffold-forming-agents. Dissolution rates of up to <20 seconds are described, with such a rapid dissolution only being achieved by means of applying mechanical forces, e.g. in the form of stirring, rubbing or massaging.

Thus, in order to be able to obtain dosage forms with even more rapid and better solubility with complete and residue-free decomposition, which decompose homogeneously and uniformly, in particular, without any mechanical influence, and which do not leave behind any swelled inhomogeneous areas in the process, and which are thus particularly suitable for the administration of cosmetic and pharmaceutical active ingredients, active and care substances, no suitable methods and compositions are so far known from the prior art.

SUMMARY OF THE INVENTION

Thus, the object of the present invention lay in providing a composition for administering active substances which is characterized by a particularly rapid solubility, wherein the dissolution was to take place completely and, if possible, without any residues, without the formation of inhomogeneous swelled areas, as well as, in particular, without any mechanical influence, and which has a dissolution behavior that is improved over known readily soluble forms of administration. Moreover, the object lay in designing these particularly rapidly and completely soluble active substance compositions in such a way that they have high mechanical strength and sufficient size in order, in particular, to be capable of being used for cosmetic or pharmaceutical application in the form of so-called single-dosage units or single-dosage applications. In this case, the compositions are supposed to be equally suited for external application as well as for an oral or peroral application.

Surprisingly, it was found that such a rapid and complete dissolution can be obtained if the dissolution behavior is subjected to a special two-stage procedure, during which the molded article is first soaked completely upon contact with the solvent or the moisturizing agent, retaining its shape for a few seconds in the process, and then decomposes into a gel while losing its physical shape. Such two-stage hydration kinetics can be obtained with freeze-dried molded article comprising a mixture of at least two recipe components, sodium alginate and magnesium ascorbyl phosphate. Additional recipe ingredients, such as cosmetic oils, such as, for example, triglycerides, jojoba oil or squalane, as well as cosmetic and pharmaceutical active substances in this case have no influence on the hydration kinetics in principle. Surprisingly, the additions of auxiliary substances such as oils can be significantly larger than the obtained quantities of alginate or magnesium ascorbyl phosphate. The oils are not an absolute requirement in order to obtain the special hydration kinetics.

It is assumed that the magnesium ascorbyl phosphate stabilizes the alginate skeleton in the composition in such a way that an additional mechanical force, caused, for example, by the hydrostatic pressure during swelling, can be absorbed for a short time. The stability equilibrium is exceeded only after complete hydration, and the molded article decomposes. Experiments with the substitution of the magnesium ascorbyl phosphate with various magnesium salts (e.g. $MgCl$, $MgSO_4$ etc), or also with mixtures of such salts with ascorbic acid or other ascorbic acid derivatives, such as ascorbyl glucoside show that this special hydration effect can only be obtained by incorporating magnesium ascorbyl phosphate.

Magnesium ascorbyl phosphate is known from the prior art as an ingredient in cosmetic preparations. For example, JP 2231496 discloses a method for freeze drying magnesium ascorbyl phosphate for cosmetic application, with a readily soluble magnesium ascorbyl phosphate powder being obtained.

Other documents, such as U.S. Pat. No. 6,458,379, DE 4002532 or JP 2004-149468 describe the use of magnesium ascorbyl phosphate in cosmetic preparations as an active substance, in particular as a skin-lightening, so-called whitening active substance.

None of the documents of the prior art mentioned describe freeze-dried pharmaceutical or cosmetic molded articles with such a specific combination of alginate and magnesium ascorbyl phosphate, which moreover are characterized by such a specific dissolution behavior.

Though FR 2886845 discloses solid preparations in the form of, for example, spheres for the application of active substances in cosmetic and pharmaceutical use, which are hydrated and dissolved prior to their application, and which can also comprise the special combination according to the invention of polymeric alginate carrier material and magnesium ascorbyl phosphate, however, the magnesium ascorbyl phosphate is present in a special form stabilized with a special maleic acid copolymer. Beyond this, no more exact information can be found in the document with regard to the actual decomposition properties and rates of the molded articles described. An "immediate dissolution" of freeze-dried compositions is specified only in connection with the exemplary embodiment 1, wherein the compositions described therein do not contain magnesium ascorbyl phosphate, but ascorbic acid. However, the special two-stage dissolution behavior cannot be obtained with ascorbic acid replacing magnesium ascorbyl phosphate, as was shown in comparative tests. The provision of a form of administration with a modified dissolution behavior is not to be considered the underlying object of FR 2886845, but rather the stabilization of the magnesium ascorbyl phosphate, which in this case is used purely as an active substance, namely as a stabilized vitamin C or ascorbic acid derivative, and not because of its hydration behavior of the molded articles that can be obtained. Suggestions as to the technical effects of magnesium ascorbyl phosphate with regard to achieving a special hydration kinetics are not apparent from FR 2886845. Moreover, the documents does not offer any information with regard to decomposition times, in particular those, that have <30 seconds, or with regard to a pH value of the preparation of >4 to be specially selected.

Freeze-dried compositions containing sodium alginate and active substances, which can be selected from the group of vitamins, In stabilized form, preferably in the form of derivatives and/or precursors of active substances, are known from WO 2008/020066. In this case, magnesium ascorbyl phosphate is mentioned as a preferred vitamin derivative. As concrete embodiments, only those are disclosed which contain sodium alginate in combination with ascorbyl glucoside. A replacement of magnesium ascorbyl phosphate with ascorbyl glucoside does not lead to the modified special two-stage dissolution behavior either, in which the freeze-dried molded article, upon being moistened, is first soaked completely while retaining its shape, and then decomposes, which was also shown in comparative tests.

WO 2009/014347 discloses small particles with a diameter of about 15 μm that are produced by spray drying, and which, as antioxidants, can contain magnesium ascorbyl phosphate as well as, for example, alginic acid as a stabilizer. A concrete embodiment containing magnesium ascorbyl phosphate and an alginate is not described. Nor is any information given with respect to the dissolution behavior of the particles according to the invention.

Therefore, the present invention provides freeze-dried molded article that contain magnesium ascorbyl phosphate and alginate, as well as, optionally, one or more active substances and/or auxiliary substances, and which are characterized by a special modified dissolution behavior because of this specific composition. Moreover, the invention also provides a method for producing these freeze-dried molded article as well as the possibility of using them in cosmetic and pharmaceutical use.

A molded article within the sense of the invention is understood to be a geometric body of a regular shape, for example, in particular, spheres, cuboids, pyramids, stars, but also molded articles replicating natural shapes, such as those in the form of animals, such as marine animals, such as starfishes, seafood, such as mussels, etc, plants and parts of plants, such as leaves etc. According to the method for producing the molded articles used according to the invention described below, all of these shapes are obtainable. Uniform spherical shapes are preferred according to the invention, such as, in particular, a spherical geometry, because it is particularly advantageous because of the particularly favorable ratio of surface area/volume. The sublimation distance through the already dry product is symmetric and small towards all sides, which facilitates vapor transport through the already dry material within the context of the freeze-drying process, thus shortening the freeze-drying process, making it more effective and inexpensive, and thus affects the stability of the molded articles obtained in a positive manner.

BRIEF DESCRIPTION OF THE DRAWINGS

The present invention will be described in greater detail with reference to the accompanying drawings in which FIGS.

1-6 schematically illustrate comparative testing carried out in accordance with the present invention.

DESCRIPTION OF THE PREFERRED EMBODIMENTS

In one aspect of the invention, a plurality of the molded articles mentioned are included in a container. This may also include mixtures of molded articles with different geometries or different sizes. The molded articles may be packaged individually, preferably, however, in particular in cosmetic application, a plurality of the molded articles lies in contact with each other next to each other in a container.

The volumes of the molded articles used are not limited as such by the method of producing them. Expediently, the volumes are preferably about 0.1 cm$^3$, preferably 0.3 cm$^3$, more preferably at least about 0.5 cm$^3$, still more preferably at least about 0.7 cm$^3$. The upper limit of the volumes used is expediently about 6 cm$^3$, preferably about 5 cm$^3$, more preferably about 4 cm$^3$. Among other things, the size of the molded articles is determined by the desired form of application or the location of the external application of the molded articles. Thus, in external cosmetic or pharmaceutical use, the application to larger body surfaces or on the hair (e.g. direct application of the moistened molded articles on the back etc., or the use as a bath preparation) makes the use of larger molded articles possible, whereas smaller molded articles are preferred during use on smaller areas of the body (e.g. the cheek, etc.).

The size can also be adapted in the production of molded articles for oral application. For example, it is conceivable to adapt the size of the molded articles to the relevant target group, wherein it is conceivable that older users are offered larger molded articles that can be handled more easily, and to offer, for example, younger users and children such molded articles that have an adapted relationship to their body size and the compliance in application to be expected because of their age.

The diameter of a molded article (maximum distance between two points in a molded article of any geometry) expediently is at least about 3 mm, preferably at least about 5 mm, more preferably at least about 7 mm, still more preferably at least about 8 mm, up to, expediently, 60 mm, preferably about 50 mm, more preferably about 40 mm, still more preferably about 30 mm.

For the aforementioned reasons, a particularly preferred molded article has a substantially spherical geometry, with the diameter of the sphere being between 3 to 30 mm, preferably between 5 and 20 mm, more preferably between 7 and 15 mm, still more preferably between 8 and 13 mm. Molded articles in the shape of a sphere with a diameter of at least 6 mm are particularly preferred.

Magnesium ascorbyl phosphate, which according to the invention is used in combination with alginate in order to achieve the special modified, two-stage hydration kinetics in the production of the freeze-dried molded articles, is a derivative of ascorbic acid (trivial name: vitamin C, (R)-5-[(S)-1,2-dihydroxyethyl]-3,4-dihydroxy-5H-furan-2-one), more specifically, a phosphoric acid monoester of ascorbic acid. Magnesium ascorbyl phosphate, compared with ascorbic acid, is characterized in particular by a higher stability with respect to light, temperature, moisture and oxidation. However, such ester derivatives also have a lower biological availability than pure ascorbic acid. Nevertheless, magnesium ascorbyl phosphate is widely used as a cosmetic active substance, in particular as a stabilized vitamin C derivative, as well as, in particular, as a skin-lightening or bleaching agent (so-called whitening). In this case, magnesium ascorbyl phosphate is added to cosmetic preparations in concentrations of, as a rule, 3-5%. A special technical effect with regard to the stabilization of scaffold-forming agents, such as alginate, or the influence on the hydration properties of dried preparations has not been described so far.

As carrier materials, the molded articles according to the invention moreover contain, from the group of hydrocolloid-forming polysaccharides, i.e. (partially) water-soluble, natural polymers that form gels or viscous solutions in aqueous systems, alginate, in particular sodium alginate.

Mixtures of alginate and other scaffold-forming agents, e.g. from the group of polysaccharides, such as carrageenan, pectins, gum tragacanth, guar gum, carob gum, agar-agar, gum arabic, pullulan, trahalose, xanthan gum, natural and modified starches, such as cationically modified starches, dextrans, dextrin, maltodextrins, chitosan, glucans, such as β-1,3-glucan or β-1,4-glucan, such as cellulose, from the group of mucopolysaccharides, such as hyaluronic acid etc, or the synthetic polymers, such as, for example, cellulose ether, polyvinyl alcohol, polyvinyl pyrrolidone, synthetic cellulose derivatives, such as methylcellulose, carboxycellulose, carboxymethylcellulose, cationically modified carboxymethylcellulose, cellulose ester, cellulose ether such as hydroxypropylcellulose, polyacrylic acid, polymethacrylic acid, poly(methylmethacrylate) (PMMA), polymethacrylate (PMA), polyethylen glycols can also be used.

With the present combination according to the invention of alginate and magnesium ascorbyl phosphate, such molded articles could surprisingly be obtained which, apart from the special mechanical stability during the rehydration process, also have an excellent stability with regard to mechanical abrasion, e.g. during handling, packaging, storage and transport, and which therefore make it possible to provide non-dusty active substance molded articles.

The alginate and optional other scaffold-forming agents which, according to the invention, are preferably used, expediently have average molar masses of about $10^3$ to about $10^8$, preferably about $10^4$ to $10^7$.

The alginates and optional other scaffold-forming agents are skin- and mucosa-compatible, and have no toxicological potential, irritating effects or other incompatibility reactions, neither during external nor in the oral or peroral application. They are pharmacologically totally harmless and thus optimally suitable for the cosmetic and pharmaceutical external and oral or peroral uses according to the invention.

The freeze-dried molded articles according to the invention can optionally contain additionally at least one or more active substances, in addition to the alginate and the magnesium ascorbyl phosphate. It should be noted in this case that magnesium ascorbyl phosphate as such also has a cosmetic and therapeutic effect and, moreover, is widely and frequently used as a cosmetic active substance. However, in the present invention, the magnesium ascorbyl phosphate is primarily used because of its special technical function in stabilizing the molded articles during the dissolution process. Thus, it should not be understood to be an active substance within the sense of the invention as claimed.

The alginates and optional other scaffold-forming agents can also have certain therapeutic effects. Thus, the scaffold-forming agent sodium alginate, which is preferably used, to a certain extent has an antiviral action, and a certain action in re-epthelization and as an antioxidant and moisturizer in skin care is ascribed to hyaluronic acid; however, they are also not to be understood to be active substances within the sense of the invention.

Active substances in particular include cosmetic or therapeutic or pharmaceutical active substances suitable for external use as well as for oral or peroral application. Preferably, the molded article used according to the invention comprises at least one cosmetic and/or pharmaceutical active substance. Accordingly, the freeze-dried molded articles according to the invention preferably are preferably cosmetic or therapeutic products.

Cosmetic molded articles or molded articles produced using cosmetic active substances within the sense of the invention are substantially products within the sense of the German Food and Feed Code (LFGB), i.e. substances or preparations from substances that are intended for external application on humans for cleaning, care or influencing appearance or body odor, or for conveying olfactory impressions, unless they are primarily intended for alleviating or eliminating disease, disorders, bodily defects or pathological complaints. In this sense, the cosmetic molded articles used according to the invention are, for example, bathing preparations, skin washing and cleansing products, skin care products, in particular facial skin care products, eye cosmetics, lip care products, nail care products, foot care products, hair care products, in particular hair washing products, hair conditioning products, hair softening rinse etc., light protection products, suntan products and skin lightening products, depigmentation products, deodorants, antihydrotics, depilatory products, insect repellents etc. or a combination of such products.

Examples of cosmetically, or optionally, for example, dermatologically therapeutically effective substances can be: anti-acne products, antimicrobial products, antitranspiration products, astringent products, deodorizing products, depilatory products, conditioning products for the skin, skin-smoothing products, products for increasing skin hydration, such as glycerin or urea, sun blockers, keratolytic products, free-radical scavengers for free radicals, antiseborrhoeic products, anti dandruff products, antiseptic active substances, active substances for treating signs of the aging of the skin and/or products modulating the differentiation and/or proliferation and/or pigmentation of the skin, vitamins such as vitamin C (ascorbic acid) and its derivatives, e.g. glycosides such as ascorbyl glucoside or esters of ascorbic acid, such as sodium or magnesium ascorbyl phosphate or ascorbyl palmitate and stearate, L-ascorbic acid phosphate esters, alkaline metal salts, such as sodium and potassium salts of L-ascorbic acid phosphate esters; earth-alkaline metal salts such as magnesium and calcium salts of L-ascorbic acid phosphate esters; trivalent metal salts such as aluminum salts of L-ascorbic acid phosphate esters; alkaline metal salts, such as sodium and potassium salts of L-ascorbic acid sulfate esters; earth-alkaline metal salts such as magnesium and calcium salts of L-ascorbic acid sulfate esters; trivalent metal salts such as aluminum salts of L-ascorbic acid sulfate esters; alkaline metal salts, such as sodium and potassium salts of L-ascorbic acid esters; earth-alkaline metal salts such as magnesium and calcium salts of L-ascorbic acid esters; and trivalent metal salts such as aluminum salts of L-ascorbic acid esters, active substances with stimulating side-effects, such as alpha-hydroxy acids, β-hydroxy acids, alpha-keto acids, β-keto acids, retinoids (retinal, retinal, retinic acids), anthralins (dioxanthranol), anthranoids, peroxides (in particular benzoyl peroxide), minoxidil, lithium salts, antimetabolites, vitamin D and its derivatives, catechins, flavonoids, ceramides, polyunsaturated fatty acids, essential fatty acids (e.g. gamma-linolenic acid), enzymes, coenzymes, enzyme inhibitors, hydrating agents, skin-soothing agents, detergents or foam-forming agents, and inorganic or synthetic matting fillers, or decorative substances such as pigments or colorants and particles for foundations, make-up formulations, and other products for cosmetic beautification and coloring of the eyes, lips and face, as well as abrasive products.

Moreover, plant substance extracts or extracts obtained therefrom or individual substances can be mentioned. Generally, the plant active substance extract is regularly selected from the group consisting of solid plant extracts, liquid plant extracts, hydrophilic plant extracts, lipophilic plant extracts, individual plant ingredients and their mixtures, such as flavonoids and its aglycones: rutin, quercitin, diosmin, hyperoside, (neo)hesperidine, hesperitine, *Ginkgo biloba* (e.g. ginkgo flavone glycosides), *Crataegus* extract (e.g. oligomer procyanidines), buckwheat (e.g. rutin), *Sophora japonica* (e.g. rutin), birch leaves (e.g. quercitin glycosides, hyperoside and rutin), elderberry blossoms (e.g. rutin), lime blossom (e.g. essential oil with quercitin and farnesol), oil of St. John's wort (e.g. olive oil extract), *calendula*, arnica, (e.g. oily extracts of the blossoms with essential oil, polar extracts with flavonoids), melissa (e.g. flavones, essential oils), immunostimulants: *Echinacea purpurea* (e.g. alcoholic extracts, fresh plant juice, press-juice), *Eleutherokokkus senticosus*; alkaloids: *Rauwolfia* (e.g. Prajmalin), *Vinca* (e.g. vincamin); other phytopharmacons: Aloe, horse chestnut (e.g. aescine), garlic (e.g. garlic oil), pineapple (e.g. bromelaines) ginseng (e.g. ginsenosides), *Silybum marianum* fruits (e.g. extract standardized to silymarin), Butcher's broom wort (e.g. ruscogenin), valerian (e.g. valepotriates, Tct. Valerianae), Kava-Kava (e.g. kavatactone), hop (e.g. hop bitter substances), Extr. passiflorae, gentian (e.g. ethanolic extract), anthraquinone-containing drug extracts, e.g. aloin-containing aloe vera juice, pollen extract, algae extract, liquorice extracts, palm extracts, galphimia (e.g. mother tincture), mistletoe (e.g. aqueous-ethanolic extract), phytosterols (e.g. beta-sitosterin), common mulleins (e.g. aqueous-alcoholic extract), drosera (e.g. liqueur-wine extract), sea-buckthorn fruits (e.g. juice obtained therefrom or sea-buckthorn oil), marshmallow root, primrose-root extract, fresh plant extracts from mallow, comfrey, ivy, horsetail, yarrow, ribwort (e.g. pressed juice), stinging nettle, celandine, parsley; plant extracts from *Norolaena lobate, Tagetes lucida, Teeoma siems, Momordica charantia* and aloe-vera extracts.

Preferred cosmetic active substances are natural and synthetic moisturizing factors, such as, e.g. glycerin, urea and ceramides, skin protection products, skin lightening products, vitamins, antioxidants, so-called anti-ageing agents, anti-irritative agents, sunblockers, etc.

In contrast to the above described molded articles, which are substantially used in cosmetics, the therapeutically used molded articles (medicaments) are such molded articles containing at least one pharmaceutical or therapeutic, in particular dermatologically active substance, and which, within the meaning of the "Arzneimittelgesetz" (German Medical Preparations Act), are intended to cure, to ease or to prevent diseases, illnesses, bodily damage or pathological complaints. Such agents or active substances are intended both for external use as well as oral or peroral application.

Active substances for external use are in particular skin-active, but also transdermal active substances. They include, for example: agents for the treatment of skin diseases, externally applicable analgesics, e.g. dextropropoxyphene, pentazocine, pethidine, buprenorphine; antirheumatics/antiphlogistics (NSAR), e.g. indomethacin, diclofenac, naproxen, ketoprofen, ibuprofen, flurbiprofen, salicylic acid and salicylic-acid derivatives such as acetylsalicylic acid, oxicams; steroid hormones, e.g. betamethasone, dexamethosone, methylprednisolone, ethynyl estradiol, medroergotamine, dihydroergotoxine; gout remedies, e.g. benzbromarone, allopurinol; external dermatological agents, including antibacterial agents, such as e.g. colloidal silver and silver salts, antimycotics, antiviral active substances, anti-inflammatory active substances, antipruritic active substances, anaesthetizing active substances, e.g. benzocaine, corticoids, anti-acne agents, antiparasitic active substances; externally applicable hormones; venous therapeutic agents; immunosuppressives etc., all for external application.

Preferred therapeutic products for external use are analgesics, e.g. immunosuppressives, hormones, products for the treatment of skin diseases such as neurodermitis, atopical dermatitis, acne, rosacea etc and anti-herpes products.

Therapeutic active substances for the oral or peroral application can be selected from the group of antihistamines, antibiotics, peptide drugs, antimycotics, bronchial therapeutics such as antiasthmatics, antitussives, mucolytics, etc., antidiabetics, such as glibenclamide, hormones, steroid hormones, such as dexamethasone, cardiac glycosides such as digitoxin, heart and circulation therapeutics such as, e.g., beta blockers, antiarrhythmics, antihypertonics, calcium antagonists etc., psychopharmaceutical agents and antidepressants, such as tricyclic antidepressants (NSMRI), serotonin-specific reuptake inhibitors (SSRI), norepinephrine reuptake inhibitors (NRI), serotonin and norepinephrine reuptake inhibitors (SNRI), monoamino oxidase inhibitors (MAO inhibitors), etc., neuroleptics, anticonvulsives or antiepileptics, hypnotics, sedatives, anaesthetics, gastro-intestinal therapeutics, lipid-lowering drugs, analgesics, such as anti-migraine agents, paracetamol, salicylic acid and its derivatives such as acetylsalicylic acid, diclofenac, ibuprofen, ketoprofen, naproxen etc, antiphlogistics, vasodilators, diuretics, antipodagric agents, cytostatic agents, muscle relaxants, plant extracts, provitamins, such as beta carotene, vitamins such as vitamin C, A, B, E etc., silica, minerals and trace elements such as, e.g., potassium, magnesium, calcium, selenium, iodine, etc., dietary supplements and food supplements etc, all for oral and peroral application.

A particularly preferred pharmaceutical active substance which is used both for external as well as oral or peroral application is salicylic acid and its derivatives, such as acetylsalicylic acid (ASS).

Preferably used active substances are, in particular, water-soluble active substances that dissolve particularly well in the aqueous mixture of alginate and magnesium ascorbyl phosphate. However, it is also possible to incorporate fat-soluble active substances. They can preferably be dissolved or dispersed in the auxiliary substances from the group of fatty substances an oils before being added to the alginate-magnesium ascorbyl phosphate mixture.

The molded articles used according to the invention furthermore optionally contain one or more auxiliary substances. Auxiliary substances include: fatty substances, such as mineral oils, such as paraffin oils or Vaseline oils, silicone oils, vegetable oils such as coconut oil, sweet almond oil, apricot oil, corn oil, jojoba oil, olive oil, avocado oil, sesame oil, palm oil, eucalyptus oil, rosemary oil, lavender oil, pine oil, thyme oil, mint oil, cardamom oil, orange-blossom oil, soybean oil, bran oil, rice oil, rapeseed oil and castor oil, wheat-germ oil and vitamin E isolated therefrom, evening-primrose oil, vegetable lecithins (e.g. soybean lecithin), sphingolipids/ceramides isolated from plants, animal oils or fats, such as tallow, lanolin, butyric oil, neutral oil, fatty-acid esters, esters of fatty alcohols such as triglycerides, and waxes with a melting point corresponding to skin temperature (animal waxes such as beeswax, carnauba wax and candelilla wax, mineral waxes, such as microcrystalline waxes, and synthetic waxes, such as polyethylene waxes or silicone waxes), as well as all oils that are suitable for cosmetic purposes (so-called cosmetic oils), such as, for example, those mentioned in the CFTA treatise entitled Cosmetic Ingredient Handbook, 1st edition, 1988. The Cosmetic, Toiletry and Fragrance Association, Inc., Washington, pH-adjusting agents, buffering substances, inorganic and organic acids or bases, surfactants in addition to the above-mentioned washing tensides, such as dispersants, emulsifiers etc, fillers, stabilizers, cosolvents, pharmaceutically and cosmetically commonly used or other colorants and pigments. In particular those that are used primarily for the color design of the molded articles and not for application and color design on the human body, such as those pigments and colorants as those decorative colorants, preserving agents, softening agents, lubricants listed in the group of active agents.

A particularly preferred auxiliary substances is selected from the group of pH-adjusting agents, preferably sodium hydroxide solution for adjusting the pH value desired according to the invention of $\geq 4$, preferably $\geq 4.5$, more preferably $\geq 5.0$, also more preferably $\geq 5.5$, still more preferably $\geq 6.0$ as well as $\geq 6.5$.

If the composition of magnesium ascorbyl phosphate and alginate and optional other active and auxiliary substances as such already has a pH value which is desired according to the invention, then of course the addition of pH-adjusting agents be dispensed with.

Other preferred auxiliary substances are those that are selected from the group of fats and oils, such as in particular from the group of cosmetic oils. Squalane is preferably selected in this case. Surprisingly, despite its hydrophobic properties, squalane causes an improved solubility of the molded article, which facilitates the external application on the skin. Apart from this, squalane also has skin-caring effects, even though it is not an active substance within the sense of the invention. Other preferred auxiliary substances from the group of fatty substances and cosmetic or pharmaceutical oils are neutral oil (triglyceride) and jojoba oil.

Generally, the classification of the above-mentioned substances into the category of auxiliary substances within the context of the present invention does not preclude these auxiliary substances from also having certain cosmetic and/or therapeutic effects, which in particular applies to the preferably used cosmetic oils mentioned.

What is crucial for the special two-stage decomposition kinetics, which is pivotal for the particularly rapid and complete residue-free dissolution of the molded articles according to the invention without mechanical influence, is the pH value of the composition. According to the invention, this is $\geq 4.0$, preferably $\geq 5.0$, more preferably $\geq 6.0$, so that a 1% by wt. solution or suspension of the molded articles according to the invention in water, at 20° C., has a pH value $\geq 4.0$, preferably $\geq 4.5$, more preferably $\geq 5.0$, also more preferably $\geq 5.5$, still more preferably $\geq 6.0$, as well as $\geq 6.5$. Surprisingly, it was found that, the higher the pH value, the faster the dissolution of the molded articles takes place.

The molded articles according to the invention serve for external cosmetic and pharmaceutical and oral or peroral use in humans and animals. External use is carried out such that the molded article according to the invention is moistened or dissolved with water or an aqueous solution containing one or more active substances and one or more auxiliary substances. Preferably, aqueous solutions are used primarily which in addition contain skin-moisturizing alcohols, such as glycerin, butylene glycol or pentylene glycol, as well as those that have a low viscosity (a viscosity <50 mPas) and no or a merely low oil content (<10% by wt based on the total composition of the aqueous solution). Moreover, such activator solutions are preferred that are free from earth-alkaline ions, such as in particular calcium and/or magnesium ions (less than 1% by wt of calcium and/or magnesium ions based on the total composition of the aqueous solution contained), as well as those having a pH value of between about pH 4.0 to 8.0.

Preferably, the molded article is placed from above on or into the surface of 0.75 to 5.0 ml of the liquid or activator solution. The liquid quantity in application can be selected as a function of the intended gel viscosity. Expediently, it is about 10 to 100 times of the weight of the sphere. For a molded article with a weight of about 50 mg, the volume of the hydration solution should be at least 0.75 ml. Retaining its external geometric shape, the molded article is in this case soaked completely with the activator solution and decomposes completely within a few seconds into a homogeneous solution or a gel. This decomposition process takes place without any external mechanical influence, for example by stirring, rubbing, squashing or massaging. Decomposition takes place within ≤30 seconds, preferably ≤20 seconds, more preferably ≤10 seconds. In a particularly preferred embodiments, this special hydration and dissolution process takes place within ≤5 seconds.

The solution of the molded article according to the invention in an amount of water suitable for a bathing application is also contained, according to the invention, in the external use. Preferably, however, application is carried out such that the molded articles are moistened and dissolved directly on the skin or hair or in a suitable container with a small quantity of about 0.5 to 5.0 ml water and a solution of active and/or auxiliary substances, the so-called activator solution, in particular with a composition as mentioned above, while forming a homogeneous and uniform residue-free solution or a gel, and are then applied in a dissolved form on the skin or hair.

The present invention also relates to a combination comprising at least one of the molded articles used according to the invention, as well as at least one aqueous activator solution containing one or more active substances and/or at least one or more auxiliary substances, in a combined spatial arrangement (application package, set, kit-of-parts etc.). The solutions of active substances can be, for example, solutions of highly volatile active and/or auxiliary substances, which should not or cannot be introduced into the molded article by freeze-drying because of the production process, such as certain parts of essential oils, perfumes, etc. Those active and/or auxiliary substances can also be contained which have a moisturizing effect which is desired and preferred in particular with regard to the external use on the skin, and which, due to this moisturizing effect or due to hygroscopic tendencies, cannot be incorporated into the freeze-dried molded article according to the invention, because its stability can be affected thereby. Moreover, it is conceivable to add to the activator solution such active and auxiliary substances that release the far more effective ascorbic acid (vitamin C) in the solution formed, or in the gel, from the magnesium ascorbyl phosphate after rehydration, by chemical conversion or other activating influences (e.g. pH shift), so that the magnesium ascorbyl phosphate also has an active substance-precursor function in addition to the stabilizing effect influencing the hydration kinetics.

The configuration of such kit-of-parts combinations of, on the one hand, a molded article according to the invention and the active substance solution, on the other hand, can provide that the two components are removed separately from the kit-of-parts arrangement and are combined and dissolved outside of it for further use. It is also conceivable, however, that a combination of the two components is carried out within the kit-of-parts packaging itself, and that the dissolved composition is then directly supplied from it to the further cosmetic or pharmaceutical external, oral and/or peroral use. Preferably, this can be done directly by the end user.

The molded articles according to the invention comprise preferably ≥5% by wt, more preferably ≥10% by wt., still more preferably ≥20% by wt., particularly preferably ≥25% by wt. magnesium ascorbyl phosphate, based on the total weight of the freeze-dried molded article.

Moreover, the molded articles according to the invention comprise preferably ≥5% by wt, more preferably ≥10% by wt., still more preferably ≥20% by wt., particularly preferably ≥25% by wt. alginate, in particular sodium alginate, based on the total weight of the freeze-dried molded article.

According to the invention, the quantity ratio of magnesium ascorbyl phosphate to alginate is preferably 0.1:1 to 5:1, preferably 0.2:1 to 3:1, more preferably 0.5:1 to 2:1.

Furthermore, the molded articles can contain up to 80% by wt. of one or more active substances, more preferably up to 40% by wt., still more preferably up to 25% by wt of one or more active substances.

Active substances from the group of vitamins are particularly preferred, such as, in particular, ascorbic acid (vitamin C) and its derivatives, and/or salicylic acid and its derivatives, such as acetylsalicylic acid (ASS) and its derivatives.

Moreover, the molded articles can contain up to about 80% by wt. of one or more auxiliary substances, preferably up to 25% by wt., more preferably up to 20% by wt. of one or more auxiliary substances.

Preferred auxiliary substances are, for example pH-adjusting agents, such as, e.g. sodium hydroxide solution, cosmetic oils, such as, e.g. squalane, jojoba oil or neutral oil, or color pigments or inert fillers.

Optionally, the molded articles also contain water residues. However, since the freeze-dried molded articles are exceptionally moisture-sensitive due to their ingredients and their inventive capability of dissolving very rapidly, the water content is to be kept as low as possible. In this case, the water content can be up to 10% by wt. The water content can change after the production of the molded article by freeze drying during storage; as a rule, it increases. Preferably, the water content of the molded article after production is maximally 10% by wt., preferably less than 5% by wt., more preferably less than 1% by wt.

A particularly preferred molded article comprises:
≥20% by wt. magnesium ascorbyl phosphate,
≥20 by wt. alginate, preferably sodium alginates, in particular low-viscosity calcium-free sodium alginate, whose 1% by wt. solution or suspension in water (1 g in 99 ml water at 20° C., pH 6-8) preferably has a viscosity of less than 2000, preferably of less than 1000, particularly preferably of less than 100 mPas,
≤50% by wt. of one or more active substances,
up to 60% by wt. of one or more auxiliary substances, such as in particular those from the group of cosmetic fats and oils, such as in particular triglycerides or pH-adjusting agents, such as inorganic bases, in particular, for example, sodium hydroxide solution, and
up to 10% by wt., preferably up to 5% by wt., more preferably less than 1% by wt. of water,
with the condition that the molded article, when liquid is added, is soaked completely, retaining its physical shape, and then decomposes completely without any mechanical influence within ≤30, preferably ≤20, more preferably ≤10, still more preferably ≤5 seconds, and that its 1% by wt. solution or suspension in water, at 20° C., has a pH value ≥4, preferably ≥4.5, more preferably ≥5.5, still more preferably ≥6.5.

Preferably, the molded article according to the invention, such as, for example, that of the above-mentioned composition, containing magnesium ascorbyl phosphate and alginate, has
- a pH value ≥4.5, more preferably ≥5.5, still more preferably ≥6.5, measured in a 1% by wt. solution or suspension of the molded article in water, at 20° C.,
- a density of 0.005 g/cm$^3$ to 0.8 g/cm$^3$ preferably 0.01 g/cm$^3$ to 0.8 g/cm$^3$,
- a volume of 0.1 cm$^3$ to 6 cm$^3$, preferably 0.6 cm$^3$ to 6 cm$^3$,
- a diameter (maximum distance between two points of the molded article) of at least 6 mm, and/or
- preferably a spherical configuration, particularly preferably the shape of a sphere.

The molded articles according to the invention constitute porous molded articles with a homogeneous distribution of the ingredients within the sense of an equal distribution of the ingredients over the entire molded article.

The molded articles according to the invention, such as, for example, those as mentioned above, are preferably dissolved with an aqueous liquid/activator solution, which comprises:
- at least 70% by wt. of water,
- at least 5% by wt. of polyalcohols,
- up to 10% by wt. of one or more active substances, such as, in particular, those from the group of the cosmetic active substances
- up to 20% by wt. of one or more auxiliary substances, such as in particular those from the group of cosmetic oils, such as in particular caprylic/capric acid triglycerides, and which has a pH value of 5-7 and, furthermore, a content of earth-alkaline ions, such as, in particular, calcium and/or magnesium ions of less than 1% by wt.

The dissolution rate of the molded articles used according to the invention is ≤30 seconds, preferably ≤20 seconds, more preferably ≤10 seconds, still more preferably ≤5 seconds, measured with molded articles having a diameter of 11 mm and a weight of 50 mg, measured by placing the molded article on a water surface. The weight ratio of water to molded article is in this case about 5:1 to 100:1. Such molded articles according to the invention show complete hydration without any recognizable non-hydrated core already after <5 seconds.

The molded articles according to the invention can be obtained by a method comprising the following steps:
(a) preparing an aqueous suspension or a solution of magnesium ascorbyl phosphate and alginate, as well as, optionally, one or more active substances and/or auxiliary substances
(b) optionally adjusting the pH value of this aqueous suspension or solution to pH >4, preferably >4.5, more preferably >5.5, particularly preferably >6.5
(c) pouring the mixture into a mold
(d) freezing the mixture in the mold, and
(e) freeze drying the frozen mixture while forming the molded article.

Optionally, other steps can be carried out between these steps; in particular, it is possible to remove the frozen molded article from the mold after step (d). Moreover, it is possible to subsequently process the surface of the frozen molded articles by mechanical processing.

Expediently, the production is carried out by first preparing an aqueous solution of the alginate and subsequently dispersing and dissolving the magnesium ascorbyl phosphate therein. Subsequently, the active substance(s) and optionally one or more auxiliary substances are added and mixed. Optionally, after mixing all of the constituents, the desired pH value is adjusted to ≥4, preferably ≥4.5, more preferably ≥5.0, also preferably ≥5.5, particularly preferably ≥6.0 as well as ≥6.5, optionally by adding the auxiliary substances from the group of pH-adjusting agents. Preferably, the pH value is adjusted by adding inorganic bases, preferably by adding sodium hydroxide solution.

The amount of the solids contained in the solution or suspension, such as the carrier material alginate and magnesium ascorbyl phosphate, as well as, optionally, further active substances and auxiliary substances, is an important influence on the density (weight of the molded article relative to the volume of the geometrical form of the molded article) of the molded article obtained. The density in turn is an important quantity for the porosity of the molded article, and thus for the dissolution rate of the molded article when moistened with water or a solution of active and/or auxiliary substances. The porous structure of freeze-dried molded articles is an essential basis for rapid solubility, because an intimate exchange between the aqueous phase and the solid molded article can occur during the rehydration process due to the large surface area in the porous material. The higher the concentration of the active substances, of the scaffold-forming agent as well as of, optionally, the auxiliary substances in the solution, the higher the density becomes, and thus, the lower the degree of porosity of the molded article and vice versa. However, the degree of porosity of the molded articles does not depend on the material density alone. Rather, material porosity is substantially a function of two parameters, the material density and the ice-crystal size. High solid contents in the aqueous suspension increase material density in the freeze-dried final product and reduce the contact surface between the rehydration agent/solid. Large freezing gradients lead to small ice crystals, which lead to large internal material surfaces, which in turn promotes rehydration. Thus, low material densities and small ice crystals are advantageous for quick moisturization and dissolution of the freeze-dried molded articles, with a certain degree of stability also being required, on the other hand, in order to obtain the special two-stage dissolution kinetics of the present invention.

Thus, apart from pure "solubility", or, in the case of polymer-based carrier substances, such as alginate, the "swelling capacity", the mechanical stability of the molded article in this case also plays a pivotal role. If the material swells too quickly, the molded article loses its physical integrity too quickly and collapses, with the molded article melting, so to speak, while moisture is added, in most cases while forming "inner" areas with a lower moisture content that have not yet swelled. The solution or gel thus obtained is inhomogeneous and has a irregular composition, accompanied by an irregular distribution of the ingredients.

However, if the stabilizing interactions within the material are too large, the material may swell while water is added, but then decomposes only under mechanical stress, such as by mechanical stirring, rubbing, squashing or massaging. A careful adaptation of the components of the recipe and the quantity ratios in the specified ranges is thus required in order to achieve, on the one hand, a sufficient mechanical strength for compensating the weight increase while swelling, and, on the other hand, a subsequent rapid hydration.

With regard to density/degree of porosity and dissolution rate, respectively, the formulation of the recipe and the production of the molded articles according to the invention, apart from the selection of the suitable quantity ratio of magnesium ascorbyl phosphate and alginate, is arranged such that the densities of the molded articles that can be obtained therewith are expediently about 0.01 g/cm$^3$ to 0.8 g/cm$^3$, preferably about 0.015 g/cm$^3$ to 0.5 g/cm$^3$, preferably about 0.02 g/cm³ to 0.2 g/cm³. The term density as it is presently used denotes the weight of the molded article relative to the volume of the exterior geometric shape of the composition.

The weight of the individual molded articles is of course dependent upon their size. Generally, the weight of the individual molded articles is about 10 to 200 mg, preferably 20 to 100 mg. For example, spheres with a diameter of 11 mm have a weight in the range from, preferably, 20 to 80 mg, more preferably 30 to 60 mg. Other preferred ranges are calculated correspondingly for spheres having other diameters.

The choice of a spherical configuration, such as, in particular, a sphere configuration, moreover has an exceptionally positive effect on the drying of the molded articles, in particular in combination with a freezing geometry in which the molded articles are frozen simultaneously from all sides at least <−20° C. Due to the beneficial surface area/volume ratio of the spherical shape, the sublimation through the product is symmetrical towards all sides and directed to small distances, which in turn facilitates vapor transport during sublimation. This method, freezing within a mold, for example by blowing with cold air, moreover reduces the proportion of non-thawable water to a minimum, so that subsequently, drying may take place at higher temperatures, which in turn reduces the costs for the freeze-drying process considerably.

Preferably, the production of the solution that is subjected to freeze-drying is carried out by first preparing a solution of the alginate and subsequently working in the magnesium ascorbyl phosphate. Then, the optionally present other active and/or auxiliary substances are worked in. If oil-soluble active substances are used, they are preferably dissolved in oils that are optionally used as auxiliary substances (in particular squalane, jojoba oil and triglycerides) and then added to the alginate-magnesium ascorbyl phosphate mixture. This production method is advantageous in that stable solutions or suspensions form in a short time. No emulsifiers or surfactants, such as tensides, are required, and no phase separation of the solution or suspension occurs during processing if oil-soluble or oily auxiliary or active substances are used.

Preferably, however, water-soluble active substances are used.

The solution or suspension thus produced preferably has a composition of 0.25-10% by wt. magnesium ascorbyl phosphate,
0.5-5% by wt, alginate,
0-20% by wt. of one or more active substances and
0-25% by wt. of one or more auxiliary substances. In each case based on the total composition of the aqueous suspension or solution.

The solution or suspension is then poured into molds which have cavities of the desired geometric shapes corresponding to the molded articles. The mold preferably consists of rubber, silicone rubber, vulcanized rubber (rubber) etc. Rubber molds are preferred. The mold materials may optionally be coated. The cavities of the molded articles into which the solution is poured generally have the shape of the desired molded article. That is, the volume of the cavity substantially corresponds to the volume of the molded article that is obtained later.

Since the volume of the solutions or suspensions filled in the cavities increases during freezing (difference in density between water and ice), the cavities are generally not filled completely. In this way, completely symmetrical molded articles are obtained. For example, this is not possible according to the method of dripping into cryogenic solutions (such as in liquid nitrogen), because in that case, unsymmetrical temperature distribution occurs, so that greater or lesser deviations from a regular form result every time. Such irregularly shaped molded articles, however, are not desired especially in the area of cosmetic final products. As a rule, this means that molded articles produced according to the dripping method require mechanical post-processing, which is not necessary according to the method as it is used according to the invention. In the case of molded articles produced with the dripping method, such post-processing becomes ever more necessary with an increasing volume of the molded article, because significant external irregularities occur in this method, which become more apparent in the case of large molded articles.

After the solution has been filled into the cavities of the mold, the solution or suspension is frozen. Cooling or freezing the solution can take place, as such, in any way, such as, for example, by blowing with cold air, cooling by applying on a plate through which cooling brine flows, or also dipping the molds into liquid gases, such as dipping into liquid nitrogen. The cooling rate in the process has an effect upon the size of the ice crystals formed. They in turn have an effect upon the pore size distribution of the molded article formed. If few large crystals are formed, then the molded article has few large pores. If many small crystals are formed, then the molded article has many small pores. The higher the cooling-off rate of the solution or suspension, the smaller the crystals become. As was already explained, freezing geometries in which the molded articles are frozen simultaneously from all sides at least <−20° C. are preferred.

The freezing temperature required depends, among other things, on how large the freezing-point lowering action of the active agents or auxiliary substances contained in the solution or suspension is. Expediently, the temperature is below the freezing point of water, down to the temperature of liquid nitrogen (−196° C.). Preferably, the freezing temperature is about −10° C. to −80° C., preferably −20° C. to −50° C. After the solution or suspension has frozen, the molded articles are removed from the mold and subjected to post-processing, if necessary. Post-processing can take place mechanically, e.g., by surface processing (grinding, roughening). The molded articles are then subjected to the freeze-drying process.

Freeze drying can take place in a manner known per se, according to generally known freeze-drying processes such as also described, for example, in DE 4328329 C2, in DE 4028622 C2 or in DE 10350654 A1.

The invention in particular includes the following preferred embodiments:

1. Freeze-dried molded article containing magnesium ascorbyl phosphate and alginate as well as optionally one or more active substances and/or auxiliary substances.
2. Freeze-dried molded article according to embodiment 1, wherein the alginate is sodium alginate.
3. Freeze-dried molded article according to any one of the embodiments 1 to 2, wherein, as an active substance, at least one is selected from the group of vitamins and their derivatives, preferably from the group of vitamin C and its derivatives.
4. Freeze-dried molded article according to any one of the embodiments 1 to 3, wherein, as auxiliary substances, at least one is selected from the group of cosmetic and/or pharmaceutical oils.
5. Freeze-dried molded article according to embodiment 4, wherein triglycerides, jojoba oil and/or squalane is selected from the group of the oils.
6. Method for producing a freeze-dried molded article according to any one of the embodiments 1 to 5, comprising the following steps:

a. preparing an aqueous suspension or a solution of magnesium ascorbyl phosphate and alginate, as well as, optionally, one or more active substances and/or auxiliary substances
b. optionally adjusting the pH value of the aqueous solution or suspension to pH >4,
c. pouring the mixture into a mold
d. freezing the mixture in the mold, and
e. freeze drying the frozen mixture while forming the molded article.

7. Method according to embodiment 6, wherein the aqueous suspension or solution from step (a) contains
0.25-10% by wt. magnesium ascorbyl phosphate,
0.5-5% by wt. alginate, preferably sodium alginate,
0-20% by wt. of one or more active substances and
0-25% by wt. of one or more auxiliary substances, in each case based on the total composition of the aqueous suspension or solution.

8. Method according to any one of the embodiment 6 to 7, wherein the pH value is adjusted in step (b) by adding inorganic bases, preferably by adding sodium hydroxide solution.

9. Method according to any one of the embodiments 6 to 8, wherein the frozen mixture from step (d) is taken out of the mold prior to the freeze drying according to step (e).

10. Freeze-dried molded article that can be obtained in accordance with the method according to any of the embodiments 6 to 9.

11. Freeze-dried molded article according to any one of the embodiments 1 to 5 and 10, whose 1% by wt. solution or suspension in water, at 20° C., has a pH value ≥4.0, more preferably ≥5.0, still more preferably ≥6.0.

12. Freeze-dried molded article according to any one of the embodiments 1 to 5 and 10 to it which decomposes completely within ≤30 seconds, preferably ≤20 seconds, more preferably ≤10 seconds, still more preferably ≤5 seconds when liquid is added.

13. Freeze-dried molded article according to any one of the embodiments 1 to 5 and 10 to 12, characterized by two-stage hydration kinetics, wherein the molded article, upon contact with a wetting liquid, absorbs it while retaining said article's physical form, and then decomposes completely, losing its physical form.

14. Freeze-dried molded article according to embodiment 13, wherein the molded article, upon contact with a wetting liquid in a weight ratio of wetting liquid to molded article of 5:1 to 100:1, absorbs it while retaining said article's physical form, and then decomposes completely, losing its physical form.

15. Freeze-dried molded article according to any one of the embodiments 1 to 5 and 10 to 14, wherein the weight ratio of magnesium ascorbyl phosphate to alginate is 0.1:1 to 5:1.

16. Freeze-dried molded article according to any one of the embodiments 1 to 5 and 10 to 15, which has a volume of 0.1 $cm^3$ to 6 $cm^3$, a density of 0.01 $g/cm^3$ to 0.8 $g/cm^3$ and/or the geometrical shape of a sphere with a diameter of at least 6 mm.

17. Use of the freeze-dried molded article according to any one of the embodiments 1 to 5 or 10 to 16 as a cosmetic agent.

18. Use of the freeze-dried molded article according to any one of the embodiments 1 to 5 or 10 to 16 as a pharmaceutical agent.

19. Use according to embodiment 17 or 18, wherein the application takes place externally on the skin and hair.

20. Use according to any one of the embodiments 17 to 19, wherein the freeze-dried molded article is moistened with water or an aqueous solution of one or more active substances and/or, optionally, auxiliary substances and decomposes without mechanical influence within ≤30 seconds, preferably ≤20 seconds, more preferably ≤10 seconds, still more preferably ≤5 seconds, and is then applied onto the skin or hair in the dissolved form.

21. Use according to embodiment 20, wherein the dissolution takes place in two stages, by
a. the molded article being completely soaked with the supplied liquid, retaining its shape in the process, and
b. then decomposing while losing its physical shape.

22. Use of the freeze-dried molded article according to any one of the embodiments 1 to 5 or 10 to 16 for the oral or peroral application of active substances.

23. Kit-of-parts combination, comprising at least one freeze-dried molded article according to any one of the embodiments 1 to 5 or 10 to 16, as well as at least one aqueous solution) comprising one or more active substances and/or, optionally, one or more auxiliary substances, in a combined spatial arrangement.

24. Use of the kit-of-parts combination according to embodiment 23 as a cosmetic agent.

25. Use of the kit-of-parts combination according to embodiment 23 as a therapeutic agent.

26. Use according to any one of the embodiments 15 to 22 and 24 to 25, which is carried out directly by the end user.

27. Use of magnesium ascorbyl phosphate for modifying the dissolution behavior of freeze-dried molded articles based on alginates.

The invention is illustrated in more detail by the following examples.

EXAMPLES

Example 1

Sodium Alginate-Magnesium Ascorbyl Phosphate Sphere, Diameter 9 mm 20 g sodium alginate are added to 960 g water with stirring, and mixed homogeneously. 20 g magnesium ascorbyl phosphate are then added with stirring, the mixture, which has a pH value of pH 6.0-8.5, is kept at a temperature of 15-25° C. in the process. The homogeneous (degassed) mixture is poured into molds, frozen through with air blowing, taken out of the mold and subsequently freeze-dried in a manner known per se.

The freeze-dried molded article contains:
50% by wt. sodium alginate
50% by wt. magnesium ascorbyl phosphate, Example 2

Sodium Alginate-Magnesium Ascorbyl Phosphate Sphere, Diameter 11 mm 30 g sodium alginate are added to 955 g water with stirring, and mixed homogeneously. 15 g magnesium ascorbyl phosphate are then added with stirring, the mixture, which has a pH value of pH 6-8.5, is kept at a temperature of 15-25° C. in the process. The homogeneous (degassed) mixture is poured into molds, frozen through with air blowing, taken out of the mold and subsequently freeze-dried in a manner known per se.

The freeze-dried molded article contains:
66.6% by wt. sodium alginate
33.3% by wt. magnesium ascorbyl phosphate, Example 3

Sodium Alginate-Magnesium Ascorbyl Phosphate Sphere, Diameter 13 mm 20 g alginate are added to 920 g water with stirring, and mixed homogeneously. 20 g magnesium ascorbyl phosphate are then added with stirring, the mixture, which has a pH value of pH 6.0-8.5, is kept at a temperature of 15-25° C. in the process. Then 40 g caprylic/capric acid triglycerides are mixed in homogeneously, and the homogeneous (degassed) mixture is then poured into molds, frozen through with air blowing, taken out of the mold and subsequently freeze-dried in a manner known per se.

The freeze-dried molded article contains:
25% by wt. sodium alginate
25% by wt. magnesium ascorbyl phosphate,
50% by wt. triglycerides Example 4

Sodium Alginate-Magnesium Ascorbyl Phosphate Sphere, Diameter 15 mm 20 g sodium alginate are added to 910 g water with stirring, and mixed homogeneously. 20 g magnesium ascorbyl phosphate are then added with stirring, the mixture, which has a pH value of pH 6.0-8.5, is kept at a temperature of 15-25° C. in the process. Then 40 g triglycerides and 10 g active substances, such as green-tea extract, are mixed in homogeneously, and the homogeneous (degassed) mixture is then poured into molds, frozen through with air blowing, taken out of the mold and subsequently freeze-dried in a manner known per se.

The freeze-dried molded article contains:
22% by wt. sodium alginate
22% by wt. magnesium ascorbyl phosphate,
44% by wt. triglycerides
11% by wt. active substances (e.g. green-tea extract)

Figure 1:
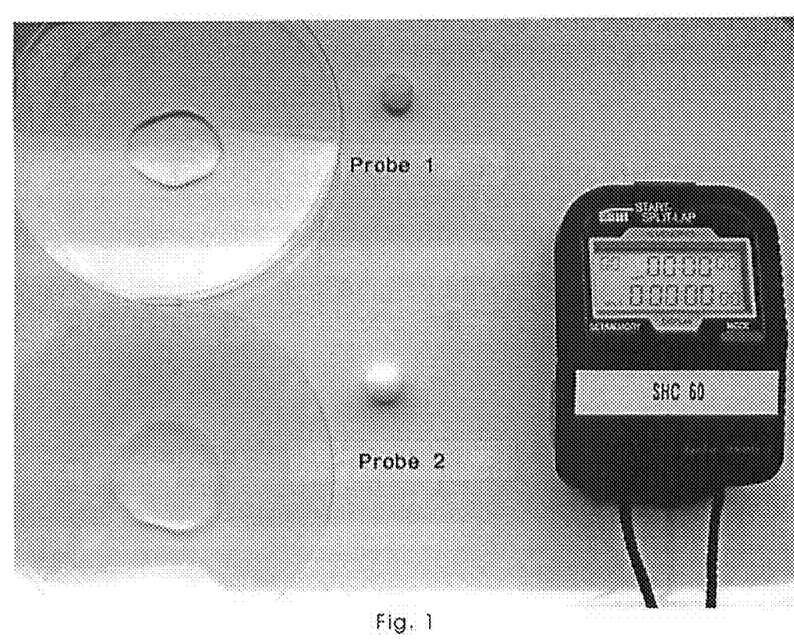

Comparative Test 1:
Dissolution Kinetics as a Function of the Recipe
Receiver: 1 ml RO water (reverse osmosis water), respectively, at approx. 20° C.
Sphere diameter: 11 mm
Sample 1: freeze-dried molded article according to the invention, according to example 3.
Sample 2: reference sample; freeze-dried molded article, produced in analogy to example 3, with magnesium ascorbyl phosphate being replaced with ascorbic acid (vitamin C).
FIG. 1 shows the configuration of the comparative test, the aqueous receiver is provided on watch glasses.

Figure 2:
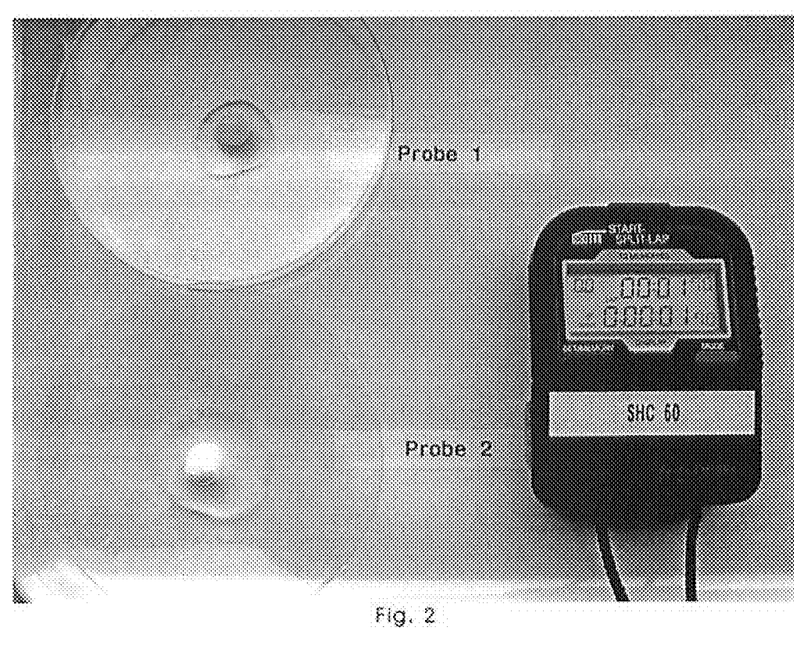

FIG. 2 shows how the sample 1 (molded article according to the invention) is completely soaked through with the water provided within the 1st second.

Figure 3:
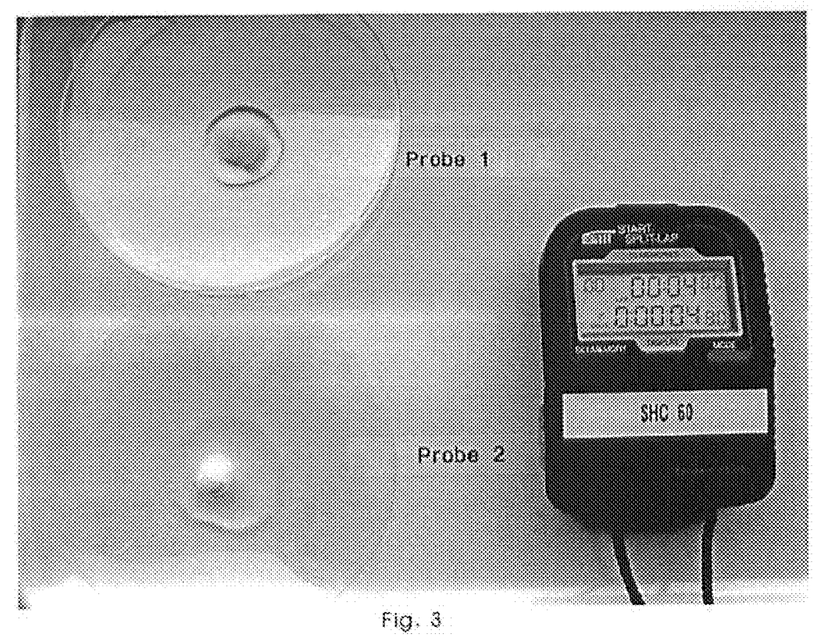

FIG. 3 further shows that after about 4 seconds, sample 1, losing structural integrity, decomposes into a completely hydrated gel without any recognizable non-hydrated areas.

Figure 4:
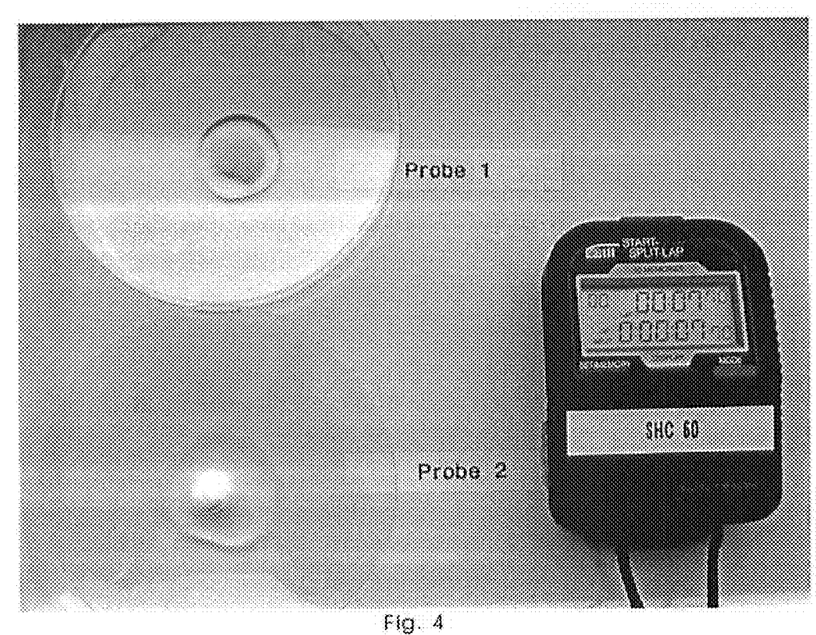
Figure 5:
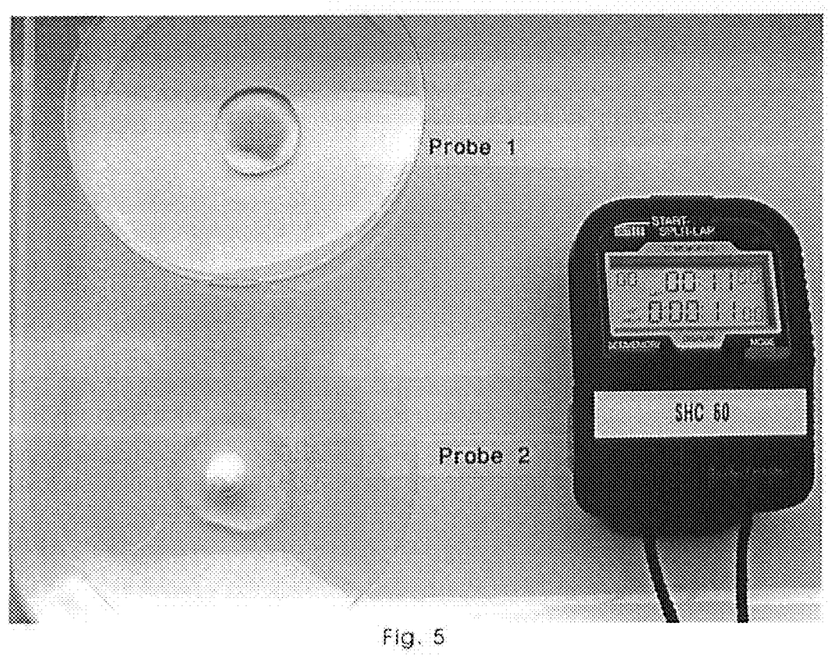
Figure 6:
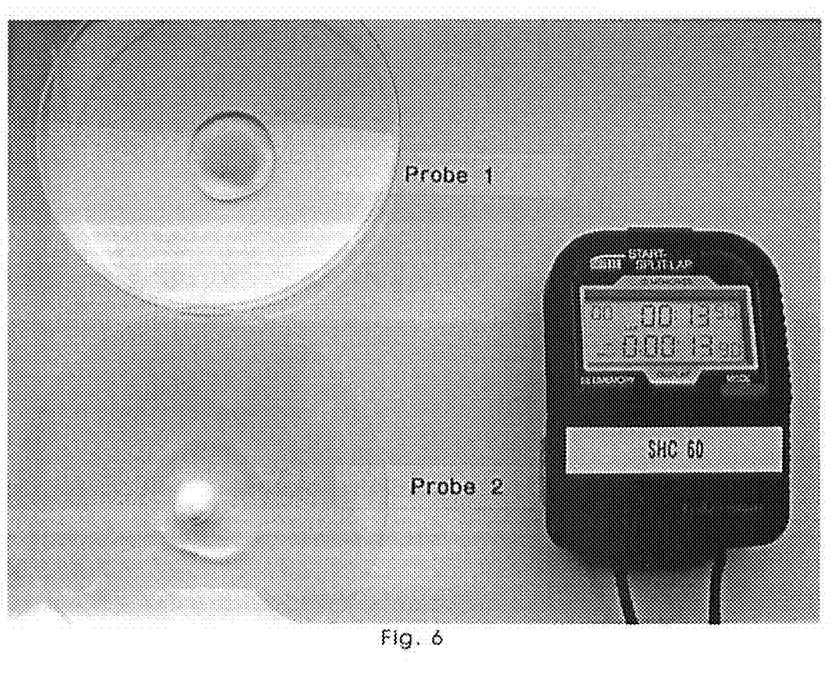

FIGS. 4 to 6 show that the comparative sample 2, with vitamin C instead of MAP, is not soaked completely through in the further course, and that it still has a top white, non-hydrated molded-article area, even after 13 seconds (FIG. 6).

The dissolution behavior shown herein is, in principle, independent of the diameter of the sphere, and basically not limited to molded articles with a diameter of 11 mm produced in accordance with example 3, but can be observed in the same way for all molded articles within the sense of this invention with different compositions and different diameters or geometric configurations.

Comparative Test 2:

In analogy to the test conditions according to comparative test 1, a comparison was additionally made of the dissolution rate and the dissolution behavior of a composition according to the invention, according to example 3, with the comparative samples in the form of the freeze-dried molded article, produced in analogy to example 3, with magnesium ascorbyl phosphate being replaced with ascorbic acid (vitamin C) or with ascorbyl glucoside. The result is shown in Table 1. It shows, that the replacement of MAP with other vitamin C compounds does not exhibit the particularly rapid dissolution behavior characterized by the two-stage Kinetics. Rather, it was shown that both the vitamin C sample as well as the ascorbyl glucoside sample showed a significantly poorer dissolution behavior. The decomposition of the molded article could not be achieved without mechanical influence, and thus, no two-stage decomposition kinetics could be observed, either.

TABLE 1

| Sample | Two-stage kinetics | Shape retention before decomposition [s] | Dissolution/ Decomposition rate [s] | Complete Dissolution/ Decomposition | Mechanical influence necessary |
| --- | --- | --- | --- | --- | --- |
| MAP | + | 1.50 | 1 | + | − |
| Vitamin C | − | — | >11 | − | + |
| Ascorbyl glucoside | − | — | >16 | − | + |

The invention claimed is:

1. A freeze-dried molded article comprising:
   (a) 10-25 wt-% magnesium ascorbyl phosphate;
   (b) 25-80 wt-% of a pharmaceutical or cosmetic oil selected from the group consisting of jojoba oil, squalene oil, caprylic/capric acid tryglycerides, and mixtures thereof; and
   (c) 20-40 wt-% calcium-free sodium alginate;
   wherein the molded article decomposes completely without mechanical influence within ≤30 seconds when added to water, and wherein the freeze-dried molded article does not comprise a maleic acid copolymer.

2. The freeze-dried molded article according to claim 1, further comprising one or more active substances.

3. The freeze-dried molded article according to claim 2, wherein at least one of the one or more pharmaceutically or cosmetically active substances is selected from the group consisting of vitamins and their derivatives.

4. The freeze-dried molded article according to claim 3, wherein the pharmaceutically or cosmetically active substance is selected from the group consisting of vitamin C (ascorbic acid) and its derivatives.

5. The freeze-dried molded article according to claim 2, wherein the one or more pharmaceutically or cosmetically active substances is selected from the group consisting of vitamin C (ascorbic acid) and its derivatives.

6. The freeze-dried molded article according to claim 1, whose 1% by wt, solution or suspension in water, at 20° C., has a pH value ≥4.0.

7. The freeze-dried molded article according to claim 6, whose 1% by wt, solution or suspension in water, at 20° C., has a pH value ≥5.0.

8. The freeze-dried molded article according to claim 7, whose 1% by wt. solution or suspension in water, at 20° C., has a pH value ≥6.0.

9. The freeze-dried molded article according to claim 1, which decomposes completely within ≤20 seconds when water is added.

10. The freeze-dried molded article according to claim 9, which decomposes completely within ≤10 seconds when water is added.

11. The freeze-dried molded article according to claim 10, which decomposes completely within ≤5 seconds when water is added.

12. The freeze-dried molded article according to claim 1, wherein the molded article contains ≥20% by wt. magnesium ascorhyl phosphate, based on the total weight of the freeze-dried molded article.

\* \* \* \* \*